United States Patent [19]
White

[11] 3,976,645
[45] Aug. 24, 1976

[54] PROCESS FOR THE PREPARATION OF 10-(HALOPHENYL)-2,3,4,10-TETRAHYDROPYRIMIDO-[1,2-a]INDOL-10-OL

[75] Inventor: Alan Chapman White, Windsor, England

[73] Assignee: John Wyeth & Brother Limited, Maidenhead, England

[22] Filed: Dec. 9, 1974

[21] Appl. No.: 530,901

[30] Foreign Application Priority Data
Dec. 20, 1973 United Kingdom............. 59064/73
Mar. 5, 1974 United Kingdom............. 9761/74

[52] U.S. Cl.................. 260/251 A; 260/326 N; 260/326.11 R; 260/326.15; 424/251
[51] Int. Cl.[2].................................. C07D 487/04
[58] Field of Search............... 260/251 A, 326.11

[56] References Cited
UNITED STATES PATENTS
3,641,147  2/1972  Topliss................... 260/562
3,850,957  11/1974  White et al. :................ 260/309.6

FOREIGN PATENTS OR APPLICATIONS
2,200,584  7/1975  Germany.................. 260/251 A
1,121,924  7/1968  United Kingdom............. 260/251 A OTHER PUBLICATIONS
Favorskaya et al., J. Gen. Chem., U.S.S.R., vol. 20, pp. 1109–1113 (1950).

*Primary Examiner*—Nicholas S. Rizzo
*Assistant Examiner*—Diana G. Rivers

[57] ABSTRACT

The invention concerns a process for preparing pyrimido[1,2-a]indoles of general formula (I)

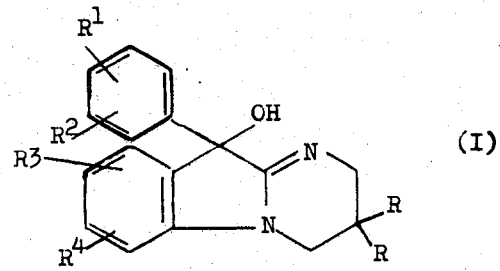

wherein R is hydrogen or lower alkyl and $R^1$, $R^2$, $R^3$ and $R^4$ are each hydrogen, hydroxyl, lower alkyl, lower alkoxy, trifluoromethyl or halogen by cyclodehydrating an indole derivative of general formula (II)

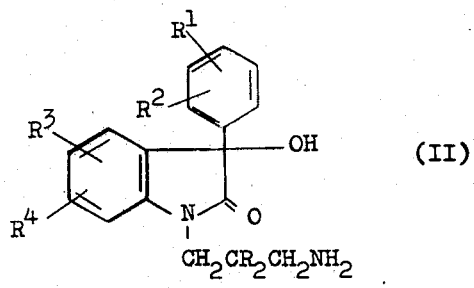

The products of formula (I) are useful as antidepressants.

2 Claims, No Drawings

PROCESS FOR THE PREPARATION OF 10-(HALOPHENYL)-2,3,4,10-TETRAHYDROPYRIMIDO-[1,2-a]INDOL-10-OL

This invention relates to a novel process for the preparation of certain pyrimido [1,2-a]indoles. The products are described in co-pending Ser. No. 361,701 filed May 18, 1973, now U.S. Pat. No. 3,891,644, by Alan C. White for "10,10-disubstituted-2,3,4,10-tetrahydro- and 1,2,3,4,10,10a-hexahydropyrimido[1,2-a]indole derivatives." U.S. Ser. No. 361,701 is a continuation-in-part of Ser. No. 211,105 filed Dec. 22, 1971 and now abandoned. The process of the present invention gives the products in good overall yield from readily available starting materials.

The present invention provides a process for the preparation of an indole derivative of the general formula (I)

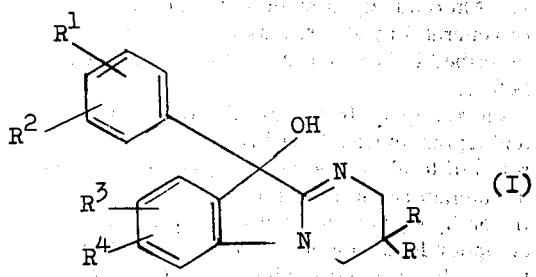

or an acid addition salt thereof, wherein R is hydrogen or lower alkyl, $R^1$, $R^2$, $R^3$ and $R^4$ are each hydrogen, hydroxyl, lower alkyl, lower alkoxy, trifluoromethyl or halogen which process comprises cyclodehydrating an indole derivative of the general formula (II)

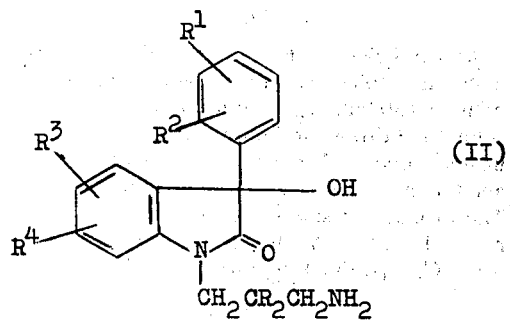

wherein R, $R^1$, $R^2$, $R^3$, $R^4$ have the meanings given above and if desired converting a resulting free base into an acid addition salt.

The term "lower" as used herein means that the radical contains up to 6 carbon atoms, preferably up to 4 carbon atoms.

The following are examples of the groups $R^1$, $R^2$, $R^3$, $R^4$: hydrogen; hydroxyl; lower alkyl such as methyl, ethyl, propyl and butyl; lower alkoxy such as methoxy, ethoxy, propoxy and butoxy; trifluoromethyl and halogen such as chlorine, fluorine and bromine. Preferred meanings of $R^1$, $R^2$, $R^3$, $R^4$ are hydrogen and halogen. R can be lower alkyl (e.g. methyl) but preferably both R groups are hydrogen.

A particularly preferred compound of general formula (I) is one in which $R^1$ is m-chloro and R, $R^2$, $R^3$ and $R^4$ are hydrogen.

The compound of general formula (II) in its free base form or as an acid addition salt thereof may be cyclodehydrated to the compound of general formula (I) by heating it, for example, in an inert organic solvent. The solvent can be, e.g. xylene or o-dichlorobenzene, and the heating can be carried out at the reflux temperature. It is preferred to carry out the cyclisation in the presence of a catalytic amount of an acid catalyst, e.g. p-toluene sulphonic acid or benzene sulphonic acid. Depending on the reaction conditions the cyclisation may be substantially complete in up to about 24 hours, e.g. up to 5 to 10 hours.

The product of general formula (I) in its free base form, can be converted into its acid addition salts, e.g. the pharmaceutically acceptable acid addition salts by standard procedures. For example, the free base can be dissolved in a suitable organic solvent and the solution treated with a solution of the selected acid, in accordance with conventional procedures for preparing acid addition salts from base compounds. As examples of suitable acids, there may be used hydrochloric, hydrobromic, tartaric, phosphoric, maleic, citric, methanesulphonic or p-toluenesulphonic acids.

The indole compounds of general formula (II) and their acid addition salts are novel compounds. We have found that these compounds can be prepared by the hydrogenation of a nitrile compound of general formula (III)

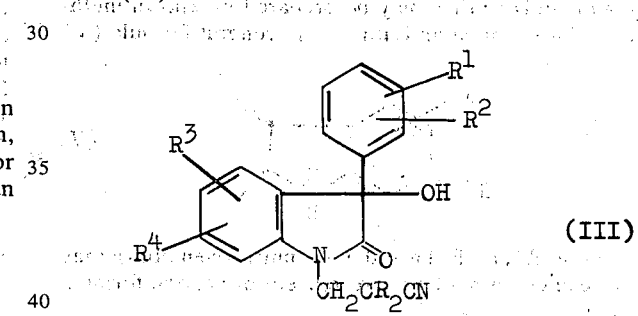

wherein R, $R^1$, $R^2$, $R^3$ and $R^4$ have the meanings given above.

The hydrogenation is carried out in the presence of a hydrogenation catalyst. Elevated temperatures and pressures may be employed. However, if the compound of formula (III) contains any substituents $R^1$, $R^2$, $R^3$ and $R^4$, such as halogen atoms, which are liable to be effected by drastic hydrogenation conditions, the hydrogenation should be carried out under mild conditions. For example, a nickel catalyst [such as Raney nickel, e.g. Raney nickel W2 (Org. Syn. Coll. Vol. III, 1955, 181)] can be employed, e.g. in presence of ammonia and ethanol, and the hydrogenation carried out at relatively low pressures (e.g. about 40 p.s.i.) and temperatures (e.g. about 40° to 50°C.).

The compound of general formula (II) can be isolated from the reaction medium by standard procedures before cyclising it to be the compound of general formula (I). The free base of general formula (II) can also be converted to its acid addition salts by procedures well known in the art, e.g. as described herein above for the preparation of the acid addition salts of the compounds of general formula (I).

Although, as mentioned above, the compounds of general formula (II) can be isolated from the hydrogenation reaction medium such isolation is not necessary if it is desired to cyclodehydrate the compounds to the compounds of general formula (I), directly.

The nitrile compounds of general formula (III) are also novel. These novel compounds can be prepared from oxindoles of general formula (IV)

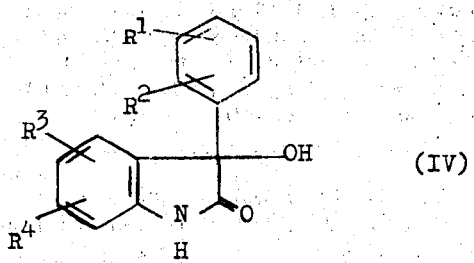

wherein $R^1$, $R^2$, $R^3$ and $R^4$ have the meanings given above. For example, a compound of formula (III) in which both R groups are hydrogen can be prepared by Michael addition of the oxindole to acrylonitrile. For example, the oxindole can be reacted with acrylonitrile in an inert solvent, preferably in presence of a basic catalyst. A particularly suitable basic catalyst is benzyltrimethyl-ammonium hydroxide (Triton B) used as a 40% solution in water. A compound of formula (III) in which both R groups are lower alkyl can be prepared by reacting the oxindole with a 3-halo-2,2-di(lower)alkyl-propionitrile in the presence of a base.

The oxindoles of general formula (IV) are known compounds or they may be prepared by known methods. For example an isatin of the general formula (V)

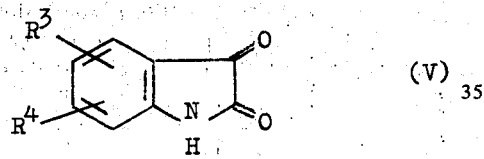

wherein $R^3$ and $R^4$ have the meanings given above may be reacted with a Grignard reagent of general formula (VI)

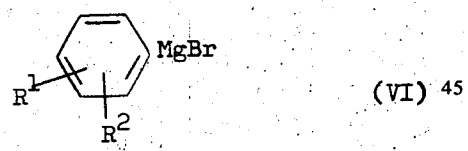

wherein $R^1$ and $R^2$ have the meaning given above, for example, by the procedure given in J. Amer. Chem. Soc., 1960, 82, 4634; J. Chem. Soc., 1961, 5558 and U.K. Specification No. 1,125,671.

The indole derivatives of general formula (II) in which R is hydrogen can be prepared by an alternative method which comprises hydrolysing a phthalimide derivative of general formula (VII)

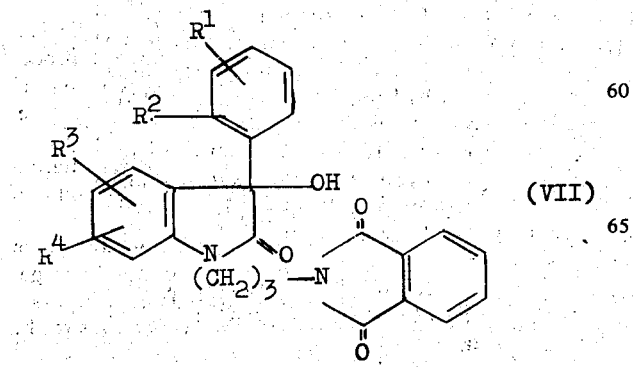

wherein $R^1$, $R^2$, $R^3$ and $R^4$ are as hereinbefore defined.

The hydrolysis of the phthalimide derivative of general formula (VII) can be carried out in the presence of, e.g. acid, base or hydrazine as in the Gabriel synthesis. We have found 40% aqueous methylamine to be of particular use.

The phthalimide derivative of general formula (VII) may be prepared by condensation of an oxindole of general formula (IV) as given above, with N-(3-halopropyl)phthalimide, e.g. N-(3-bromopropyl)phthalimide. The condensation can be effected in presence of a basic catalyst such as sodium hydride in, for example an organic solvent e.g. dimethylformamide or toluene.

The compounds of formula (I) possess an asymmetric carbon atom and hence optical enantiomorphs are possible and the compounds may be obtained as the pure enantiomorphs or mixtures of such enantiomorphs, such as the racemates. The pure enantiomorphs may be obtained by the process of the present invention by employing optically active starting materials. Alternatively, a racemic mixture of the compound of general formula (I) may be resolved by the process described in U.S. Ser. No. 361,701 referred to hereinbefore.

The compounds of general formula (I) are useful as antidepressants as described in U.S. Ser. No. 361,701, referred to above. Some compounds also possess anti-inflammatory, anti-histaminic, cardiovascular, diuretic or hypoglycaemic activity. Particularly important compounds having good antidepressant activity when tested by standard pharmacological tests include 2,3,4,10-tetra- hydro-10-phenyl-pyromido 1,2-a]indol-10-ol and 10-(m-chlorophenyl)-2,3,4,10-tetrahydropyrimido[1,2-a]indol-10-ol.

The following examples illustrate the invention:

EXAMPLE 1

3-(m-Chlorophenyl)-1-(2-cyanoethyl)-3-hydroxyindolin-2-one.

Acrylonitrile (1.06 g.) was added to a solution of 3-(m-chlorophenyl)-3-hydroxyindolin-2-one (2.6 g.) in ethanol (50 ml.) containing Triton B (40% aqueous solution, 3 drops) and the resulting mixture stirred and heated under reflux for 6 hours. Charcoal was added and the mixture filtered and evaporated to about 15 ml. The product crystallised as colourless prisms 1.57 g., m.p. 149°-50°. (Analysis: Found C, 65.5; H, 4.4; N, 8.8%. $C_{17}H_{13}ClN_2O_2$ requires C, 65.3; H, 4.2; N, 8.9%).

EXAMPLE 2

1-(3-Aminopropyl)-3-(m-chlorophenyl)-3-hydroxyindolin-2-one.

The nitrile of Example 1 (1.57 g.) was reduced at 40 p.s.i. and 40°C in the presence of Raney Nickel W2 (2.g.) in absolute ethanol half saturated with dry ammonia (50 ml.). Uptake ceased when slightly more than 2 equivalents of hydrogen had been taken up. The catalyst was filtered off, the ethanol solution evaporated to leave a green oil which gave 1.22 g. microcrystals, m.p. 250°-252°(decomp), of 1-(3-aminopropyl)-3-(m-chlorophenyl)-3-hydroxyindolin-2-one hydrochloride on treatment with isopropanol and hydrogen chloride in dry ether.

EXAMPLE 3

10-(m-Chlorophenyl)-2,3,4,10-tetrahydropropyrimido[1,2-a]indol-10-ol.

The hydrochloride of Example 2 (1.44 g.) was converted to the base and then heated under reflux with stirring in xylene (50 ml.) containing p-toluenesulphonic acid (50 mg.) in an apparatus fitted with a water separator. After 4 hours the reaction was cooled and the product crystallised to give the title compound as off-white rhombs, m.p. 190°–192°C.

EXAMPLE 4

1-(3-m-Chlorophenyl)-3-hydroxy-1-(3-phthalimidopropyl)indolin-2-one 3-(m-Chlorophenyl)-3-hydroxy-indolin-2-one (5.2 g.) in dry DMF (25 ml.) was added dropwise to a stirred suspension of sodium hydride (60% dispension in oil, 0.96 g) in DMF (50 ml.) keeping the temperature at 10°C. The mixture was stirred at room temperature for 1 hour. N-(3-bromopropyl)phthalimide (5.6 g.) in DMF (20 ml.) was added dropwise at 10° to 15°C. and the resulting mixture left stirring at room temperature overnight. The reaction mixture was poured into water and extracted with toluene. After drying the solvent was removed to leave an oil which afforded 4.24 g. of crystals, m.p. 169°–171°C, from methanol. (Found: C, 67.6; H, 4.5; N, 6.3. $C_{22}H_{19}ClN_2O_4$ requires C, 67.2; H, 4.3; N, 6.3%).

EXAMPLE 5

1-(3-Aminopropyl)-3-(m-chlorophenyl)-3-hydroxyindolin-2-one

The phthalimido compound from Example 4 (1.0 g.) was dissolved in aqueous methylamine (40%, 30 ml.) and left at room temperature for 24 hours. The solution was evaporated under reduced pressure until an oil came out of solution. The solution was extracted with chloroform, the extracts dried and evaporated to an oil which afforded 0.76 g. of the title compound as the hydrochloride, m.p. 245°–246°C. (decomp), on treatment with isopropanol and ethereal hydrogen chloride.

EXAMPLE 6

Reaction of acrylonitrile with 3-hydroxy-3-phenylindolin-2-one by a procedure analogous to that of Example 1 gives 1-(2-cyanoethyl)-3-hydroxy-3-phenylindolin-2-one Hydrogenation of the 1-(2-cyanoethyl)-3-hydroxy-3-phenyl-indolin-2-one by a procedure analogous to that of Example 2 gives 1-(3-aminopropyl)-3-hydroxy-3-phenyl-indolin-2-one. Cyclodehydration of 1-(3-aminopropyl)-3-hydroxy-3-phenylindolin-2-one by a procedure analogous to that of Example 3 gives 2,3,4,10-tetrahydro-10-phenylpyrimido [1,2-a]indol-10-ol.

EXAMPLE 7

Reaction of acrylonitrile with 5-chloro-3-phenyl-3-hydroxyindolin-2-one by a process analogous to that of Example 1 gives 5-chloro-1-(cyanoethyl)-3-hydroxy-3-phenylindolin-2-one. Hydrogenation of the 5-chloro-1-(2-cyanoethyl)-3-hydroxy-3-phenylindolin-2-one by a procedure analogous to that of Example 2 gives 1-(3-aminopropyl)-5-chloro-3-hydroxy-3-phenylindolin-2-one. Cyclodehydration of the 1-(3-aminopropyl)-5-chloro-3-hydroxy-3-phenylindolin-2-one by a procedure analogous to that of Example 3 gives 8-chloro-2,3,4,10-tetrahydro-10-phenylpyrimido [1,2-a]indol-10-ol.

EXAMPLE 8

Reaction of acrylonitrile with 3-hydroxy-3-(m-tolyl)indolin-2-one by a procedure analogous to that of Example 1 gives 1-(2-cyanoethyl)-3-hydroxy-3-(m-tolyl)indole-2-one. Hydrogenation of 1-(2-cyanoethyl)-3-hydroxy-3-(m-tolyl) indolin-2-one by a procedure analogous to that of Example 2 gives 1-(3-aminopropyl)-3-hydroxy-3-(m-tolyl)indolin-2-one. Cyclodehydration of 1-(3-aminopropyl)-3-hydroxy-3-(m-tolyl)indolin-2-one by a procedure analogous to that of Example 3 gives 2,3,4,10-tetrahydro-10-(m-tolyl)pyrimido[1,2-a]indol-10-ol.

EXAMPLE 9

Reaction of acrylonitrile with 3-(m-fluorophenyl)-3-hydroxyindolin-2-one by a procedure analogous to that of Example 1 gives 1-(2-cyanoethyl)-3-(m-fluorophenyl)-3-hydroxyindolin-2-one. Hydrogenation of 1-(2-cyanoethyl)-3-(m-fluorophenyl)-3-hydroxyindolin-2-one by a procedure analogous to that of Example 2 gives 1-(3-aminopropyl)-3-(m-fluorophenyl)-3-hydroxyindolin-2-one. Cyclodehydration of 1-(3-aminopropyl)-3-(m-fluorophenyl)-3-hydroxyindolin-2-one by a procedure analogous to that of Example 3 gives 10-(m-fluorophenyl)-2,3,4,10-tetrahydropyrimido[1,2-a]indol-10-ol.

EXAMPLE 10

Reaction of acrylonitrile with 3-(3,4-dichlorophenyl)-3-hydroxyindolin-2-one by a procedure analogous to that of Example 1 gives 1-z-cyanoethyl)-3-(3,4-dichlorophenyl)-3-hydroxyindolin-2-one. Hydrogenation of 1-(2-cyanoethyl)-3-(3,4-dichlorophenyl)-3-hydroxyindolin-2-one by a procedure analogous to that of Example 2 gives 1-(3-aminopropyl)-3-(3,4-dichlorophenyl)-3-hydroxyindolin-2-one. Cyclodehydration of 1-(3-aminophenyl)-3-(3,4-dichlorophenyl)-3-hydroxyindolin-2-one by a procedure analogous to that of Example 3 gives 10-(3,4-dichlorophenyl)-2,3,4,10-tetrahydropyrimido[1,2-a]indol-10-ol.

EXAMPLE 11

Reaction of acrylonitrile with -3-(m-anisyl)-3-hydroxyindolin-2-one by a process analogous to that of Example 1 gives 1-(2-cyanoethyl)-3-(m-anisyl)-3-hydroxy-indolin-2-one. Hydrogenation of the 1-(2-cyanoethyl)-3-(m-anisyl) 3-hydroxy-indolin-2-one by a procedure analogous to that of Example 2 gives 1-(3-aminopropyl)-3-(m-anisyl)-3-hydroxy-indolin-2-one. Cyclodehydration of the 1-(3-aminopropyl)-3-(m-anisyl)-3-hydroxy-indolin-2-one by a procedure analogous to that of Example 3 gives 10-(m-anisyl)-2,3,4,10-tetrahydro-pyrimido[1,2-a]indol 10-ol.

EXAMPLE 12

Reaction of acrylonitrile with 3-hydroxy-3-(m-trifluoromethylphenyl)-indolin-2-one by a process analogous to that of Example 1 gives 1-(2-cyanoethyl)-3-hydroxy-3-(m-trifluoromethylphenyl)indolin-2-one. Hydrogenation of the 1-(2-cyanoethyl)-3-hydroxy-3-(m-trifluoromethylphenyl)indolin-2-one gives 1-(3-aminopropyl)-3-hydroxy-3-(m-trifluoromethylphenyl)indolin-2-one. Cyclodehydration of 1-(3-aminopropyl)-3-hydroxy-3-(m-trifluoromethylphenyl)indolin-2-one by a procedure analogous to that of Example 3 gives 10-(m-trifluoromethylphenyl)-2,3,5,10-tetrahydropyrimido [1,2-a]indol-10-ol.

I claim:

1. A process for the preparation of a 10-(m-halophenyl)-2,3,4,10-tetrahydropyrimido[1,2-a]indol-10-ol comprising a. hydrogenating a 3-(m-halophenyl-1-(2-cyanoethyl)-3-hydroxyindol-2-one at a temperature of about 40° to 50°C. and a pressure of about 40 p.s.i., in the presence of a nickel catalyst and ammonia to give a 1-(3-aminopropyl)-3-(m-halophenyl)-3-hydroxyindol-2-one, and b. heating a 1-(3-aminopropyl)-3-(m-halophenyl)-3-hydroxyindol-2-one in an inert organic solvent to give the 10-(m-halophenyl)-2,3,4,10-tetrahydropyrimido-[1,2-a]indol-10-ol.

2. A process according to claim 1 wherein the halo substituent is chloro.

* * * * *